US012343712B2

(12) United States Patent
Krajczynski et al.

(10) Patent No.: US 12,343,712 B2
(45) Date of Patent: Jul. 1, 2025

(54) STEAM AUTOCLAVE PROCESS CHAMBER AND THE METHOD OF PRODUCING THE STEAM AUTOCLAVE PROCESS CHAMBER

(71) Applicant: ENBIO TECHNOLOGY SP. Z O.O., Gdynia (PL)

(72) Inventors: Marek Krajczynski, Gdynia (PL); Maciej Chmielak, Gdynia (PL)

(73) Assignee: ENBIO TECHNOLOGY SP. Z O.O., Gdynia (PL)

( * ) Notice: Subject to any disclaimer, the term of this patent is extended or adjusted under 35 U.S.C. 154(b) by 731 days.

(21) Appl. No.: 17/605,161

(22) PCT Filed: May 8, 2020

(86) PCT No.: PCT/PL2020/000044
§ 371 (c)(1),
(2) Date: Oct. 20, 2021

(87) PCT Pub. No.: WO2020/242324
PCT Pub. Date: Dec. 3, 2020

(65) Prior Publication Data
US 2022/0203316 A1  Jun. 30, 2022

(30) Foreign Application Priority Data
May 27, 2019 (PL) .......................................... 430050

(51) Int. Cl.
*A61L 2/00* (2006.01)
*A21B 1/00* (2006.01)
(Continued)

(52) U.S. Cl.
CPC . *B01J 3/04* (2013.01); *A61L 2/07* (2013.01); *A61L 2202/122* (2013.01); *B22D 19/0072* (2013.01)

(58) Field of Classification Search
CPC .... A61L 2202/14; A61L 2202/15; A61L 2/06; A61L 2/07; A61L 9/03
(Continued)

(56) References Cited

U.S. PATENT DOCUMENTS 4,637,916 A * 1/1987 Hennebert .............. A61L 2/204
422/27
5,303,325 A * 4/1994 Pasternak ............. F24H 3/0405
219/541

FOREIGN PATENT DOCUMENTS

| EP | 1 021 207 B1 | 4/2002 |
| EP | 1 867 344 A1 | 12/2007 |

(Continued)

OTHER PUBLICATIONS

International Search Report issued by the European Patent Office for International Patent Application No. PCT/PL2020/000044, mailed Aug. 13, 2020.
(Continued)

*Primary Examiner* — Monzer R Chorbaji
(74) *Attorney, Agent, or Firm* — Myers Wolin, LLC

(57) ABSTRACT

A steam autoclave process chamber in the form of an open metal tank fitted with the necessary technical means to fix the closing lid and to connect the necessary accessories characterised in that there is at least one heater (4) inside the tank walls (1,2,3), where the heater is integrally incorporated with the wall into a single inseparable element. A method of producing a steam autoclave process chamber which consists in the making of an open metal tank with walls in the form of a single casting of any desired shape under a known casting method, followed by subsequent stages which involve mechanical machining of the casting and fitting it with necessary chamber accessories.

10 Claims, 3 Drawing Sheets

(51) Int. Cl.
  *A61L 2/07* (2006.01)
  *B01J 3/04* (2006.01)
  *F24D 15/02* (2006.01)
  *B22D 19/00* (2006.01)

(58) Field of Classification Search
  USPC .......... 422/292, 307; 219/400; 392/379, 368
  See application file for complete search history.

(56) References Cited

FOREIGN PATENT DOCUMENTS

| GB | 1561913 A | 3/1980 |
|---|---|---|
| WO | 99/33497 A1 | 7/1999 |
| WO | 2016/016857 A1 | 2/2016 |

OTHER PUBLICATIONS

Preliminary Report on Patentability with written opinion issued by the European Patent Office for International Patent Application No. PCT/2020/000044, mailed Aug. 13, 2020.

* cited by examiner

STEAM AUTOCLAVE PROCESS CHAMBER AND THE METHOD OF PRODUCING THE STEAM AUTOCLAVE PROCESS CHAMBER

CROSS REFERENCE TO RELATED APPLICATIONS

The present application is a U.S. National Phase of International Patent Application Serial No. PCT/PL2020/000044, filed on May 8, 2020, which claims priority to Polish Application P.430050, filed on May 27, 2019, the contents of each of which are incorporated by reference in their entirety for all purposes

FIELD OF THE INVENTION

The invention relates to a steam autoclave process chamber and the method of producing a steam autoclave process chamber. It is designated for the construction of autoclaves of various types, especially of class B, i.e. autoclaves with fractionated pre-vacuum.

BACKGROUND

Known are many different methods, systems, and devices designed for carrying out the sterilisation processes. Depending on their designation, place of application, the required parameters, and materials subject to the sterilisation process they differ in their structure and working principle. Sterilisation processes may be achieved by various methods, using ultrasounds, electric current, heat, radiation, plasma, or chemical substances. One of the sterilisation methods is thermal sterilisation with pressurised saturated steam, using an autoclave, which is a device fitted with a heated closed pressure tank with a lid, steam generator with the necessary fixtures, and the remaining equipment, such as measuring instruments, regulation, control, and monitoring systems, and safety systems. The closed tank serves as the process chamber inside which the air is replaced with steam. Typically, the steam sterilisation processes take place at the temperatures of 121° C. and 134° C. To optimise the sterilisation process in steam autoclaves it is important for the process chamber walls to heat quickly and precisely up to the temperature of the sterilisation process in progress, which is of particular importance in top class autoclaves, i.e. class B autoclaves. The temperature of the process chamber walls must not be lower than the temperature of the process, so that the steam filling the chamber does not condensate on the walls. This is because steam condensation makes it necessary to supplement the steam, which affects the stability, effectiveness, and duration of the process. At the same time the temperature of the chamber walls must not be too high, since this would heat up the steam and increase the pressure inside the chamber, which must not be allowed.

The autoclave process chambers known to date take the form of metal tanks of various shapes and structures, which may be fitted with other elements depending on the needs, such as heating elements of various forms, installed at the tank walls. Most frequently used heating elements are resistance heaters in contact with chamber walls, where the heaters take the form of wires, tapes, or plates with appropriate insulation ensuring good electric insulation from the chamber walls, and at the same time high heat transmission. Used in the known structures of cuboid autoclave chambers are various types of flat heaters, such as micanite or silicone heating elements, pressed against the external surface of the chamber walls so as to guarantee the largest area of contact and thus achieve the best heat transfer parameters while ensuring good electric insulation from the metal chamber walls.

The known methods of producing process chambers involve stage one when an open metal tank is produced under any of the known technologies: casting as a single element, welding individual walls together, etc. Then, in the subsequent stages the tank is fitted with other necessary elements, such as inlet/outlet stub pipes, fixing elements to install the door/lid, etc.; it is also then that the heating elements are installed, if required. In general, process chambers are cylindrical or cuboid in shape, and the cylindrical tanks are most frequently made under the welding and pressing technologies, while the casting technology works best for cuboid tanks.

Known from patent publication EP1021207B1 is a sterilisation device having a housing which encases a process chamber and other elements necessary for the sterilisation process. The process chamber is a double-wall tank, where the space between its internal and external walls is filled with fluid, demineralised water in particular. The water is heated by the heating elements immersed therein, in the bottom part of the tank, where the same heating elements allow to obtain stable temperature of the tank walls and generate steam in the top part of the tank, whereupon the steam is injected into the sterilisation chamber via a valve. The device is also fitted with a water tank, pump, valves, and control elements.

Disclosed in European patent application EP1867344A1 is an autoclave having a process chamber in the form of a tank with a door fitted on hinges, a water-filled boiler, and a heating element which generates steam, as well as other necessary accessories. On the external wall of the process chamber tank there is an electric heater to heat the chamber walls.

Known from international patent application WO9933497A1 is an autoclave process chamber with a heating device fixed on its external wall, where the heating device consists of a number of thermistor heating elements of a special structure, featuring flat metal surfaces for thermal and electric contact. On both sides of the heating elements there are insulation plates made of a material which transmits heat but insulates electrically, preferably ceramic plates. On the side of the thermistor, the plates are coated with a layer of conductive metal, which may serve as the electrodes of the heating element. The external surfaces of the insulation plates contact directly the radiators made of a material characterised by high heat transmission and electric conductivity parameters, such as aluminium. The shapes of both radiators are aligned with the shape of the chamber walls and are designed so as to ensure possibly best heat transmission between the heating element and the chamber wall.

In the known methods of producing steam autoclaves with heated walls, the first stage consists in producing a metal pressure tank of the desired shape under any of the known methods: welding, pressing, or casting. In the subsequent stages the tank is fitted with necessary accessories, such as lid fixing elements, connection stub pipes and the remaining fittings, as well as the heating elements at the chamber walls.

A disadvantage of the known solutions of an autoclave chamber with heated walls consists in the slow transfer of heat from the heater to the wall, which makes the entire process longer, whereas increasing the power so as to accelerate the process results in fast wearing of the heaters and the need to replace them frequently.

SUMMARY

The steam autoclave process chamber in the form of an open metal tank fitted with the necessary technical means to fix the closing lid and to connect the necessary accessories according to the invention is characterised in that there is at least one heater inside the tanks walls, where the heater is integrally incorporated with the wall forming a single inseparable element.

Preferably, the chamber takes the form of a cast cuboid tank, where there is a pipe heater inside each of the two larger parallel side walls and where the ends of the heater pipes extend outside the tank, while on the back wall are connection stub pipes extending outside the tank.

In a preferable variant, each of the pipe heaters is wavy in shape, with a number of straight sections running parallel to one pair of the edges of the larger side walls, where the straight sections are interconnected with arches.

Especially preferably, the larger side walls are thinner in the areas in between the pipe heater route, and the wall surfaces on the inside of the tank are flat.

In a preferable variant, the larger side walls have ribs shaped on their external sides, where the ribs run perpendicular to the straight sections of the pipe heater.

Most preferably, the pair of ribs located the closest to the tank opening extends outside the cuboid contour of the tank casting, and is higher than the other ribs inside the cuboid contour of the tank casting.

In one of the variants, there are two mounting holes made in one of the larger side walls, each opening within a different rib, and four mounting legs, two per each rib, while made in the back wall there is only one mounting opening and additional mounting protrusions.

Preferably, formed on each of the larger side walls of the chamber are additional positioning protrusions.

In a preferable variant, there are extending tabs shaped on the smaller side walls, on the side of the tank opening.

The method of producing the steam autoclave process chamber according to the invention, which consists in the making of an open metal tank with walls in the form of a single casting of any desired shape under a known casting method, followed by subsequent stages which involve mechanical machining of the casting and fitting it with necessary chamber accessories is characterised in that before the casting is initiated, there is at least one pipe heater placed in the casting mould so that it is found inside the cast wall of the tank, and that the ends of the heater pipes extend outside the casting mould, whereupon the mould is filled with molten metal in which the pipe heater gets sunk.

Preferably, made at the casting stage are also connection stub pipes and tabs for mounting the lid, all integrated into a single element with the tank walls, whereupon the tabs are drilled through in the mechanical machining process.

The autoclave chamber and its production method according to the invention solve the problem of heating up the process chamber walls to the desired temperature swiftly, and of keeping the temperature stable, thus shortening the sterilisation process and extending the failure-free life of the process chamber.

BRIEF DESCRIPTION OF THE DRAWINGS

An invention embodiment is illustrated in the drawing, where.

DETAILED DESCRIPTION OF THE PREFERRED EMBODIMENTS

Figure 1:
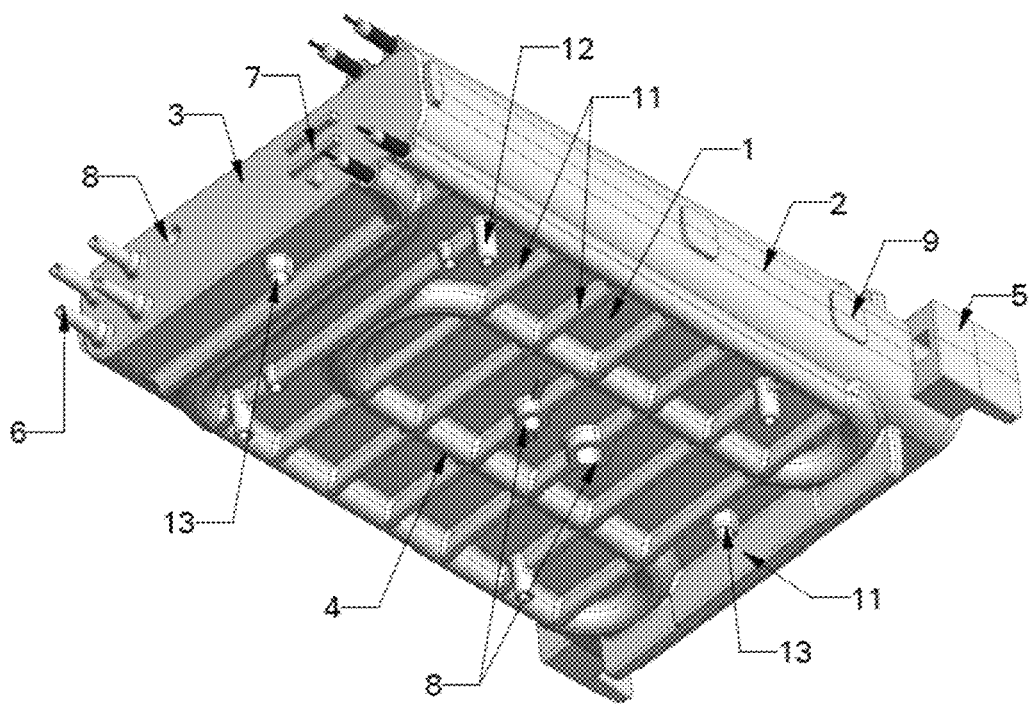
FIG. 1 shows the view of the chamber from the side of the back wall and one of the larger side walls.
Figure 2:
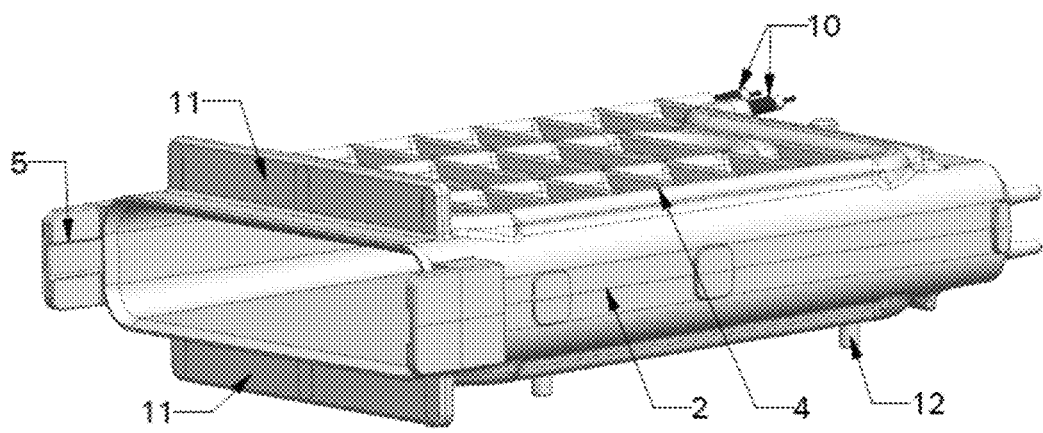
FIG. 2 shows the chamber from the side of its opening.
Figure 3:
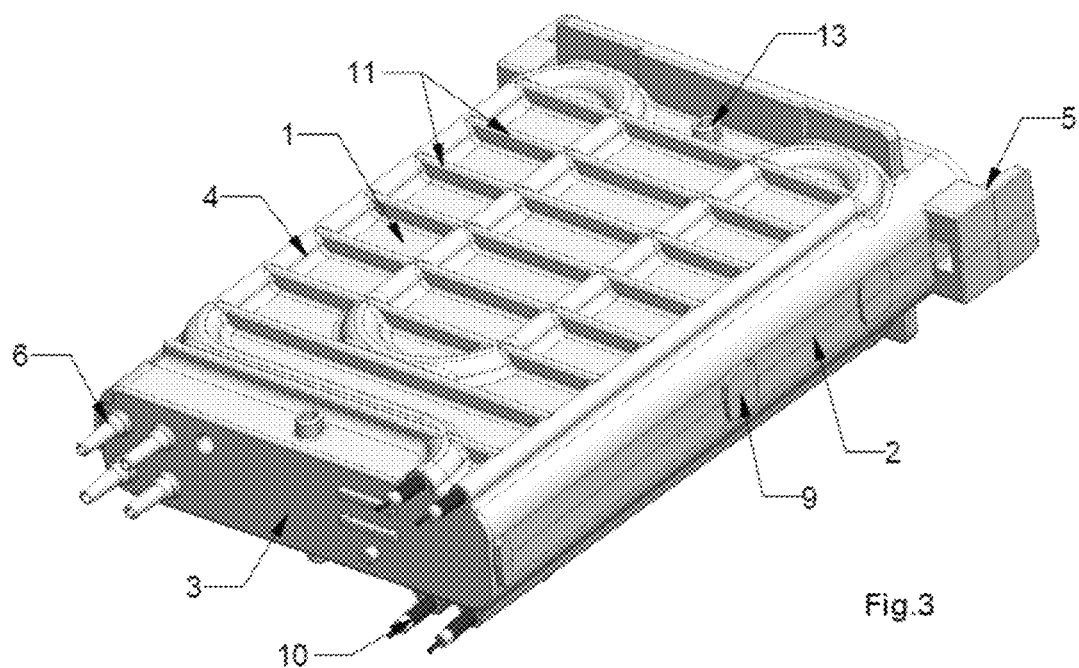
FIG. 3 presents the view of the chamber from the side of the back wall and the other larger side wall.
Figure 4:
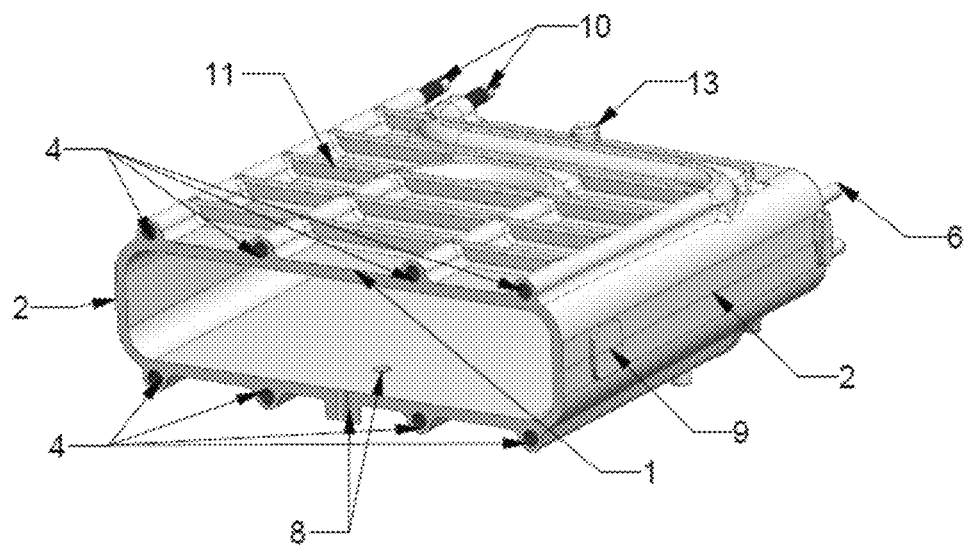
FIG. 4 shows the chamber in cross section.

The exemplary steam autoclave chamber, as shown in FIG. 1, FIG. 2, FIG. 3, FIG. 4, takes the form of a cuboid metal tank open on one side, having two parallel larger side walls 1, two parallel smaller side walls 2, and a back wall 3. Sunk inside each of the larger side walls 1 is one pipe heater 4. Shaped on the smaller side walls 2 on the side of the chamber opening are tabs 5, one extending from each of those walls, intended for the mounting of the lid which closes the chamber, which is not shown on the drawing. Shaped on one side of the back wall 3 are four connection stub pipes 6 which extend outside the contour of the cuboid, and additional mounting protrusions 7 intended for the mounting of a thermal trip. All walls 1, 2, 3 of the chamber tank, together with the sunk pipe heaters 4, extending tabs 5, and connection stub pipes 6 make up a single integrated element in the form of a casting. The holes drilled through in the connection stub pipes 6 are used to connect: a pressure sensor, safety valve, Hepa filter, and chamber outlet. In addition, the back wall 3 features one mounting hole 8 intended for the installation of a process sensor. The holes and notches in the tabs 5, and the small protrusions 9 shaped on the smaller side walls 2 enable the locking and sealing of the chamber lid, as well as the assembly and movement of special guides. On the side of the tank opening, the edges of all side walls 1, 2 are beveled in a specific way so as to match the lid and ensure chamber tightness under overpressure and negative pressure. Each of the pipe heaters 4 is of a known structure of a steel pipe incorporating a resistance wire immersed in powder serving as an insulator, with ends protected with ceramics and silicone. The pipe heater 4 sunk in one larger side wall 1 is shaped into a wave with four regularly distributed straight sections parallel to the longer sides of those walls, where the straight sections are interconnected with arched sections, and where one of the final straight sections unfolds into a section parallel to the shorter side of that side wall so that its end is found side by side the end of the second final straight section. The other pipe heater 4, sunk in the second larger side wall 1, is a mirror reflection of the first heater, and the ends 10 of the two pipe heaters 4 extend outside the contour of the casting cubicle by the back wall 3, on the side opposite to the connection stub pipes 6. All walls of the tank casting which forms the chamber are flat on the tank inside. The thickness of the larger side walls 1 varies and is the largest in places where the pipe heater 4 runs, and smallest in the areas in between the heater, where the side walls, on their external side, also feature a number of ribs 11, parallel to one another and to the shorter side of that wall, and thus perpendicular to the straight sections of the pipe heater 4. The ribs 11 serve as a reinforcing element and prevent deformation of the autoclave process chamber when the autoclave is working. The pair of ribs 11 which is located closest to the chamber inlet is higher than the other ribs and may serve as an additional protection against deformation of the beveling on the edges of the opening, it may also be used for mounting elements of the outer casing.

The remaining ribs 11 are lower and do not extend outside the cuboid contour of the chamber, and in places where they run the thickness of the chamber is the same as in places where the pipe heater 4 runs. Shaped in one of the larger side walls 1 are two mounting holes 8, each made in a different rib 11, one of which is designated for the connection of a steam generator, and the other for a revision plug; also shaped thereon are four mounting legs 12, two per rib. Moreover, formed on the external side of each of the larger side walls 1 are two additional positioning protrusions 13 which facilitate positioning of the wall for the mechanical machining of the casting. In the exemplary embodiment the casting of the chamber tank is made of aluminium, and its approximate dimensions are as follows: larger walls 200 mm×300 mm, smaller walls 300 mm×50 mm, and the back wall 200 mm×50 mm. The wall thickness ranges from 5 mm to 10 mm.

The method of producing the steam autoclave process chamber in the exemplary embodiment is made up of the following main stages: making of an open cuboid metal tank under a known casting method in an pre-prepared casting mould of any desired shape, drilling the necessary holes in the casting and beveling the tank edges on the side of the opening under a CNC machining method, mounting external elements which constitute the necessary accessories of the process chamber. The casting mould is given the shape which allows for the ready casting to have four connection stub pipes 6 integrated with the back wall 3 of the tank into a single element and extending outside the contour of the cuboid, and to have tabs 5 in the shape of letter L extending from the smaller side walls 2 on the side of the tank opening. At the first stage, before the casting mould is filled with molten metal, two pipe heaters 4 are placed inside the mould, each inside one of the larger side walls 1 of the tank, so that the insulated ends 10 of the pipe heaters extend outside the casting mould on the same side, by the back wall 3 of the tank. Preferably, the casting mould is given a shape which allows for the larger side walls 1 of the tank to be thinner in areas outside the route of the pipe heaters 4 and to have transverse ribs 11 formed parallel to the shorter side of these walls. Then, the casting mould is filled with molten metal, especially with AL, to obtain an aluminium casting of a cuboid open tank, where in the two parallel larger walls 1 of the tank pipe heaters 4 are sunk forming a single element with these walls, as shown in FIG. 1, 2, 3. The ready casting of the tank is subject to computer-controlled machining so as to give the edges of the tank opening the desired geometry, drill the holes in the connection stub pipes 6 and make all remaining necessary mounting holes 8: one in the back wall 3 and two in one of the larger side walls 1, as well as the holes in the tabs 5 extending from the smaller side walls 2, which enable the mounting, locking, and sealing of the tank lid. Used to position the tank casting during the CNC machining are four additional positioning protrusions 13, two on each of the larger side walls 1, formed at the casting stage. At the last stage, the tank is fitted with a closing lid and with the necessary process chamber accessories, not shown on the drawing: on the back wall 3: chamber outlet, pressure sensor, safety valve, Hepa filter—for the connection stub pipes 6, process sensor in the mounting opening 8 and a thermal trip between special mounting protrusions 7, and on one of the larger side walls 1—revision plug in one of the mounting opening 8, and a steam generator connection in the other mounting opening 8.

Figure 5:
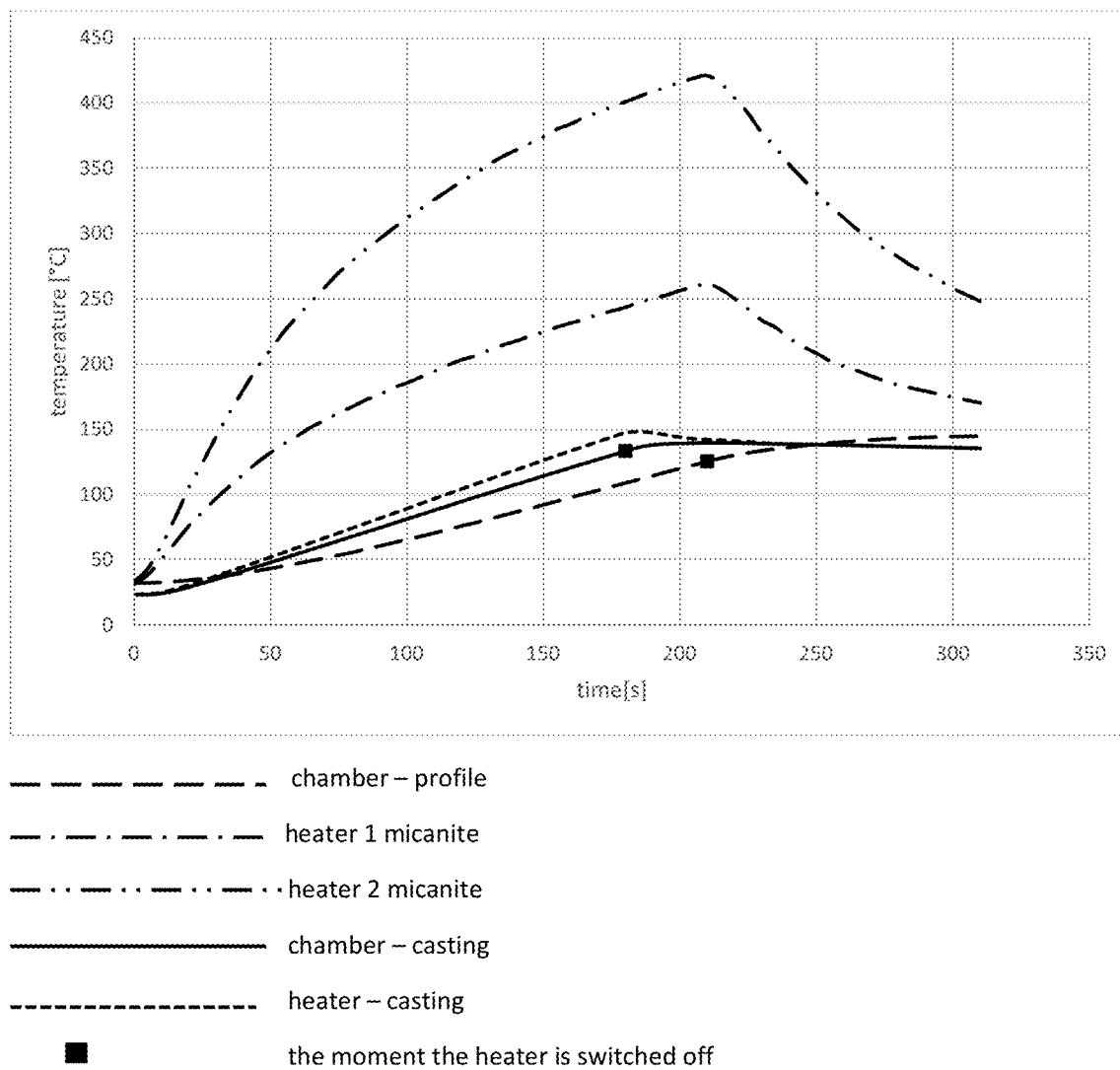
FIG. 5 shows comparative temperature graphs as a function of time.

As shown in FIG. 5, the solution according to the invention ensures much better thermal and time parameters than the known solution in which side walls of a chamber are heated with micanite-insulated flat heaters placed thereon. In an exemplary known solution employing a micanite heater, it takes approximately 215 seconds for the chamber walls to reach the required process temperature of 134° and the heater to switch off, where it is necessary to heat one of the heaters to more than 250°, and the other to more than 400°. In the solution according to the invention which employs a heater sunk inside the chamber walls, the chamber walls reach the required process temperature of 134° and the heater switches off after approximately 180 seconds, where the heater sunk in the casting is heated up to the temperature of no more than approximately 150°, which is only slightly higher than the required temperature of the chamber walls. The solution according to the invention guarantees the best possible contact between the heater surface and the walls of the process chamber, and thus the fastest transfer of heat to the walls of the process chamber. This makes it possible to substantially accelerate the heating up of the chamber, sizably reduce the necessary power of the heaters, achieve far better temperature distribution across the chamber walls and precise control over wall temperature. At the same time the failure-free life is extended, without the need to replace the heaters, because they work in a comfortably low temperature which is only slightly higher than the temperature of the chamber walls.

The invention claimed is:

1. A steam autoclave process chamber in the form of an open metal tank comprising technical means to fix a closing lid and to connect process chamber accessories, wherein there is at least one heater (4) inside tank walls (1,2,3) where the heater (4) is integrally incorporated with the wall forming a single inseparable element, wherein
    each of the pipe heaters (4) is wavy in shape, with a number of straight sections running parallel to one pair of edges of larger side walls (1), where straight sections are interconnected with arches, wherein
    on both sides of the heating elements of the at least one heater (4) there are insulation plates located which contact directly radiators made of aluminium, and wherein
    the each of the pipe heaters (4) is sunk in a molten metal inside each of two larger parallel side walls (1), and wherein
    ends (10) of the heater pipes extend outside the tank, while on a back wall (3) connection stub pipes (6) are extending outside the tank.

2. The chamber according to claim 1, wherein the larger side walls (1) are thinner in areas between the route of the pipe heater (4), and wherein surfaces of the side walls from an inside of the tank are flat.

3. The chamber according to claim 2, wherein the larger side walls (1) have ribs (11) shaped on their external sides, where the ribs run perpendicular to the straight sections of the pipe heater (4).

4. The chamber according to claim 3, wherein a pair of ribs (11) located the closest to a tank opening extends outside a cuboid contour of the tank casting, and is higher than the other ribs (11) inside the cuboid contour of the tank casting.

5. The chamber according to claim 3, wherein there are two mounting holes (8) made in one of the larger side walls (1), each opening within a different rib (11), and four mounting legs (12) made two per each rib (11), while in a back wall (3) there is one mounting opening (8) made and additional mounting protrusions (7).

6. The chamber according to claim 5, wherein formed on each of the larger side walls (1) are additional positioning protrusions (13).

7. The chamber according to claim 1, wherein there are tabs (5) shaped on smaller side walls (2), on a side of the tank opening, one extending from each of the smaller side walls (2).

8. The chamber according to claim 1, wherein on a side of a tank opening the edges of side walls (1,2) are bevelled to match the closing lid and ensure chamber tightness under overpressure, and wherein one of the final straight sections of the pipe heaters (4) unfolds into a section parallel to a shorter side of that side wall so that its end is found side by side the end of a second final straight section.

9. A method of producing a steam autoclave process chamber consisting of:
- making of an open cuboid metal tank with walls in the form of a single casting of any desired shape under a known casting method
- drilling holes in the casting
- mechanical machining of the casting
- fitting the casting with chamber accessories
- placing, before the casting is initiated, at least one pipe heater (4) in the casting mould so that the at least one pipe heater (4) is found inside a cast wall of the tank, and that ends (10) of the heater pipes extend outside the casting mould, and
- filling the mould with molten metal in which the pipe heater (4) gets sunk inside each of two larger parallel side walls (1), wherein each of the pipe heaters (4) is wavy in shape, with a number of straight sections running parallel to one pair of edges of larger side walls (1), where straight sections are interconnected with arches, wherein on both sides of heating elements of the at least one heater (4) there are insulation plates located which contact directly radiators made of aluminium, wherein on a back wall (3) connection stub pipes (6) are extending outside the tank, wherein the larger side walls (1) have ribs (11) shaped on their external sides, where the ribs run perpendicular to the straight sections of the pipe heater (4), wherein on a back wall (3) there is one mounting opening (8) made and additional mounting protrusions (7), wherein on each of the larger side walls (1) there are additional positioning protrusions (13) located, and wherein there are extending tabs (5) shaped on smaller side walls (2).

10. The method according to claim 9, wherein the method further consists of:
- integrating into a single element with the tank walls (1, 2, 3), connection stub pipes (6) and tabs (5) made at the casting stage for mounting the lid, and
- drilling the tabs through in the mechanical machining process.

* * * * *